(12) United States Patent
Borden

(10) Patent No.: US 10,541,047 B2
(45) Date of Patent: Jan. 21, 2020

(54) HEALTHCARE INTERNET SERVICE PROVIDER PROXY

(71) Applicant: MRO Corporation, Norristown, PA (US)

(72) Inventor: David J. Borden, Merion, PA (US)

(73) Assignee: MRO Corporation, King of Prussia, PA (US)

( * ) Notice: Subject to any disclaimer, the term of this patent is extended or adjusted under 35 U.S.C. 154(b) by 1027 days.

(21) Appl. No.: 14/619,591

(22) Filed: Feb. 11, 2015

(65) Prior Publication Data

US 2015/0227696 A1    Aug. 13, 2015

Related U.S. Application Data

(60) Provisional application No. 61/938,342, filed on Feb. 11, 2014.

(51) Int. Cl.
| | |
|---|---|
| *G06F 21/00* | (2013.01) |
| *G16H 10/60* | (2018.01) |
| *G06Q 10/10* | (2012.01) |
| *H04L 29/08* | (2006.01) |
| *H04L 12/58* | (2006.01) |
| *G06F 19/00* | (2018.01) |

(52) U.S. Cl.
CPC ............ *G16H 10/60* (2018.01); *G06F 19/00* (2013.01); *G06Q 10/107* (2013.01); *H04L 51/08* (2013.01); *H04L 51/12* (2013.01); *H04L 51/24* (2013.01); *H04L 51/34* (2013.01); *H04L 67/2819* (2013.01)

(58) Field of Classification Search
CPC ....... G06F 19/322; H04L 51/08; H04L 51/24; H04L 51/12; H04L 67/2819; H04L 51/34; G06Q 10/107
See application file for complete search history.

(56) References Cited

U.S. PATENT DOCUMENTS

| | | | |
|---|---|---|---|
| 8,935,753 B1 * | 1/2015 | Cha | G06Q 50/22 709/207 |
| 2007/0106754 A1 * | 5/2007 | Moore | G06F 17/3089 709/217 |
| 2009/0164253 A1 * | 6/2009 | Lyshkow | G06F 19/321 705/3 |
| 2011/0078570 A1 * | 3/2011 | Larsen | G16H 10/60 715/710 |

\* cited by examiner

*Primary Examiner* — Kendall Dolly
(74) *Attorney, Agent, or Firm* — Lauletta Birnbaum LLC

(57) ABSTRACT

A Health Information Service Providers Proxy (HISP Proxy) for Electronic Medical Records (EMR)-focused and Non-EMR focused environments for healthcare organizations (HCOs) to manage their Direct Secure Messaging (DSM) and HISP communications is disclosed. The HISP Proxy includes a DSM message bus located between HCO end-users and a HISP to intercept inbound messages and outbound messages and then to pass the messages through, an Accounting Service, a Privacy Policy Service, a Document Distribution Service, a Message Disposition Notifications (MDN) Alerting Service, and/or a Document Signing Service.

16 Claims, 10 Drawing Sheets

HEALTHCARE INTERNET SERVICE PROVIDER PROXY

CROSS-REFERENCE TO RELATED APPLICATIONS

This application claims priority to U.S. Provisional Patent Application No. 61/938,342 filed on Feb. 21, 2014.

STATEMENT REGARDING FEDERALLY SPONSORED RESEARCH OR DEVELOPMENT

The present invention was not developed with the use of any Federal Funds, but was developed independently by the inventor.

BACKGROUND

1. Field

The invention relates to a HISP Proxy for EMR-focused and Non-EMR focused environments for HCOs to manage their DSM and HISP communications

2. Background

Under the Health Insurance Portability and Accountability Act of 1996 (HIPAA), healthcare providers are not permitted to transmit PHI (Protected Health Information) by regular (i.e., non-secure) e-mail; they are, however, permitted to fax this information. This has resulted in a large dependence upon faxing for communication of PHI, which is highly inefficient and costly.

DSM (Direct Secure Messaging) means a technology created by the Office of the National Coordinator for Health Information Technology (ONC) to provide a low-cost, low-complexity path to electronic sharing of patient medical information by healthcare providers. It is a form of secure e-mail that adheres to additional protocols and standards. Companies that provide the infrastructure backbone for DSM are called Health Information Service Providers, or HISPs.

The federal government has made it a requirement for certified EMRs to be able to provide DSM and to interoperate with HISPs, beginning in 2014. There are many HISPs operating in the United States as of the end of 2013.

DSM is a form of secure e-mail, but it differs from normal Internet secure e-mail in the following respects:

Identity Vetting: In normal Internet secure e-mail, a user can easily obtain an e-mail address, or endpoint. In DSM, users must be Identity Vetted in order to obtain a DSM endpoint.

Closed Network: In normal Internet secure e-mail, any e-mail Internet Service Provider (ISP) can relay messages to any other ISP. In DSM, Healthcare Internet Service Providers (HISPs) can only relay messages to other HISPs with whom they have an established trust relationship. This trust relationship is enforced by an exchanged certificate, known as a Trust Anchor. HISPs may exchange Trust Anchors individually, in a peer-to-peer manner; or Trust Anchors may be bundled and shared among groups of HISPs that subscribe to a common Trust Policy or federation.

Message Disposition Notifications (MDNs): In normal Internet e-mail, MDNs may be provided by receiving systems to let senders know that their messages were received, but this is an optional requirement, and most regular e-mail systems do not provide this feature. In DSM, due to the potentially critical nature of the messages being sent and received, HISPs are required to provide MDNs.

Referring now to FIG. 1, there are a number of problems facing healthcare organizations (HCOs) using DSM, as HCOs transition to using DSM. Such, HCO's may have managed disclosure or an Release of Information Process 150 and an Unmanaged Disclosure process 152 through the healthcare enterprise Some of these problems are systemic, affecting the HCO at a compliance and health information management (HIM) level. Others are technical issues of interfacing hospital systems with HISPs. Still others are user convenience issues, which nevertheless are critical to the successful use of DSM.

Accounting of Disclosures: HCOs are required to be able to provide a patient, upon request, with an Accounting of Disclosures of their PHI. Tracking disclosures and keeping a comprehensive log of this across the HCO enterprise has been a major problem facing HIM departments even before DSM, and DSM will greatly exacerbate and complicate this problem.

Restrictions on Disclosures: HCOs are required to comply with state and federal law, as well as (to some degree) the wishes of the patient, in how, what, and to whom they disclosure PHI. Ensuring that the flow of PHI through DSM complies with all application disclosure restrictions is another challenge for HCOs who wish to use DSM.

Recipient Communication Preferences: Although DSM is expected to become prevalent in healthcare communications over the next five years, it is by no means assured that all recipients of PHI will have DSM mail accounts, or will prefer to receive PHI by this method. Some may prefer fax, and others would prefer to receive mail in their regular e-mail account. Furthermore, communications with non-healthcare providers, such as patients and others with an interest in receiving health information are not expected to have DSM mailboxes. Having to manage multiple methods of distributing information is a taxing problem for HIM within the hospital today, and DSM complicates this problem.

Message Disposition Notifications (MDNs): DSM standards require that e-mail return receipts be sent when mail is delivered and additional when the mail is picked up from the recipient's mailbox. In the DSM world, these receipts are referred to as Message Disposition Notifications, or MDNs. Because these are required, end-users get bombarded with these MDNs, and by default they simply come into the inbox, which leaves end-users with the problem of connecting them with the messages in the sent box that they refer to. Because of the critical nature of the information that is contained in these messages, it is essential that end-users can easily and clearly know the disposition of the messages that they are sending. Without this ease of use, the value of the entire DSM system could be undermined.

Document Signing: Some HCOs interact with individual healthcare providers, both outside and within their organization, by generating orders that require electronic signatures. A natural use case for DSM is to allow these documents to be easily shared and signed electronically. Creating a process to affix e-signatures to medical orders, and doing so with an underlying communication mechanism that is compliant with federal rules for privacy, security, and electronic signatures, is a highly complex technical problem that is beyond the scope of most HCOs to implement on their own.

Microsoft Exchange Integration: DSM can be accessed by users through EMRs, and the DSM standards specify SOAP-based web services as the preferred method for this. However, DSM messages can also be created, sent, and received through more traditional e-mail methodologies, provided that the security and privacy standards are met, through a combination of technical constraints and operational policies and procedures. These traditional methodologies include browser-based WebMail, and web client software using S-SMTP and S-POP, and IMAPI.

Some HCOs, especially those that use e-mail management servers such as Microsoft Exchange to manage their internal user's e-mail communications, may wish to integrate their internal e-mail accounts with their DSM e-mail accounts. It happens that the security requirements of HISP servers are not compatible with the type of authentication that Microsoft Exchange is capable of being configured with, and this poses a problem for these HCOs who wish to manage all e-mail communication, DSM and otherwise, through a common e-mail server platform.

While the applicability of DSM to healthcare organizations is potentially great, DSM itself falls into a continuum of methodologies, used for disclosing PHI to entities outside of the HCO. DSM is intended primarily for sharing data among healthcare providers, and secondarily for sharing PHI between providers and payers (both public, such as CMS, Medicare, and Medicaid, as well as private-sector commercial insurers).

There is a broad spectrum of other entities outside the hospital to which health information must be disclosed on a regular basis, including patients, courts and attorneys, health registries, government agencies, and the like. Within an HCO, the HIM department is traditionally tasked with fulfilling this function, known as Release-of-Information or ROI; this manually intensive work is often outsourced to 3rd party ROI service providers.

Whether performed internally by HIM, or by outside service providers under the management of HIM, the ROI function is governed by an array of Federal and State laws and regulations, and must conform to hospital disclosure management policy. Two of the key components of compliance are maintaining an Accounting of Disclosures; and preventing restricted disclosures from taking place. Restrictions on disclosures include prohibitions spelled out in law, as well as consent restrictions made explicitly by the patient to the hospital.

SUMMARY

A HISP Proxy for EMR-focused and Non-EMR focused environments for HCOs to manage their DSM and HISP communications. The HISP Proxy includes a DSM message bus located between HCO end-users and a HISP to intercept inbound messages and outbound messages and then to pass the messages through, the DSM Message Bus having an interior interface having a SOAP server interface and an S-SMTP/S-POP/IMAPI interface to interface with DSM users, an email relay to interface with other non-DSM users, an exterior interface to interface with the HISP and that mimics the interface behavior of a SOAP client or an S-SMPT/S-POP/IMAPI client, a Service Bus in communication with the interior interface and the exterior interface to allow an ordered chain of functional service components to be executed as messages pass through the DSM Message Bus. Also included is a an accounting service to provide HIPAA Accounting of Disclosures (AoD), the accounting service parses outbound message attachments to determine an identity of a patient whose information is being disclosed and records patient related data for the AoD in a database, a privacy policy service to provide compliance with disclosure restrictions, privacy policy service is configured with hospital policy and tracks patient restrictions, and a document distribution service that receives the documents to be distributed and then sends the documents to an intended recipient via DSM, Fax, Email notification with a secure pickup link, or an Exception queue.

An MDN alerting service may be provided that allows a sending end-user to configure preferences for when they wish to be alerted when messages have taken too long to be delivered to or read by their intended recipient.

A document signing service may also be provided that enables patient health record documents to be sent to clinicians for electronic signature, internal and external message channels are used for a signing request message, depending on whether the signing user is within the HCO or outside.

The document distribution service may include a provider directory to match recipients with their preferred method of receiving messages.

The DSM message bus may include a DSM accounts manager to keep track of DSM user accounts and account configuration data, and allows authentication to take place on the interior interface and the exterior interface. The DSM message bus may also include a certificate manager to manage and keep secure End-User Level certificates. The DSM message bus may further include an Inbound channel and an Outbound channel for transmitting message traffic between the DSM users and the HISP, and the internal channel and the external channel transmit meta-communications for service-specific purposes.

An e-mail management server interface may be provided to map regular organizational e-mail accounts with DSM e-mail accounts, provided by the HISP Proxy's Email Relay component.

The accounting system may further include a healthcare document parser to read metadata associated within documents that are passed as attachments or within XDR messages.

BRIEF DESCRIPTION OF THE DRAWINGS

The embodiments will be described in detail with reference to the following drawings in which like reference numerals refer to like elements wherein.

DETAILED DESCRIPTION

Referring now to FIGS. 3-10, the system of the present invention comprises a HISP Proxy for HCOs to manage their DSM and HISP communications.

1. HISP Proxy

The HISP Proxy 10 is a system for HCOs to manage their DSM and HISP communications in a way that: Complies with Accounting of Disclosures rules and restrictions on disclosures; Integrates with existing HIM systems and public databases for managing this accounting and these restrictions; Provides a single pathway for messages to be distributed to recipients who have different preferences for how they wish to receive communications; Helps end-users manage MDNs and know when messages have failed to reach their intended target within a given amount of time; Facilitates a secure and compliant way of electronically signing medical orders; and Addresses technical challenges of integrating internal e-mail systems such as Microsoft Exchange with DSM.

Figure 1:
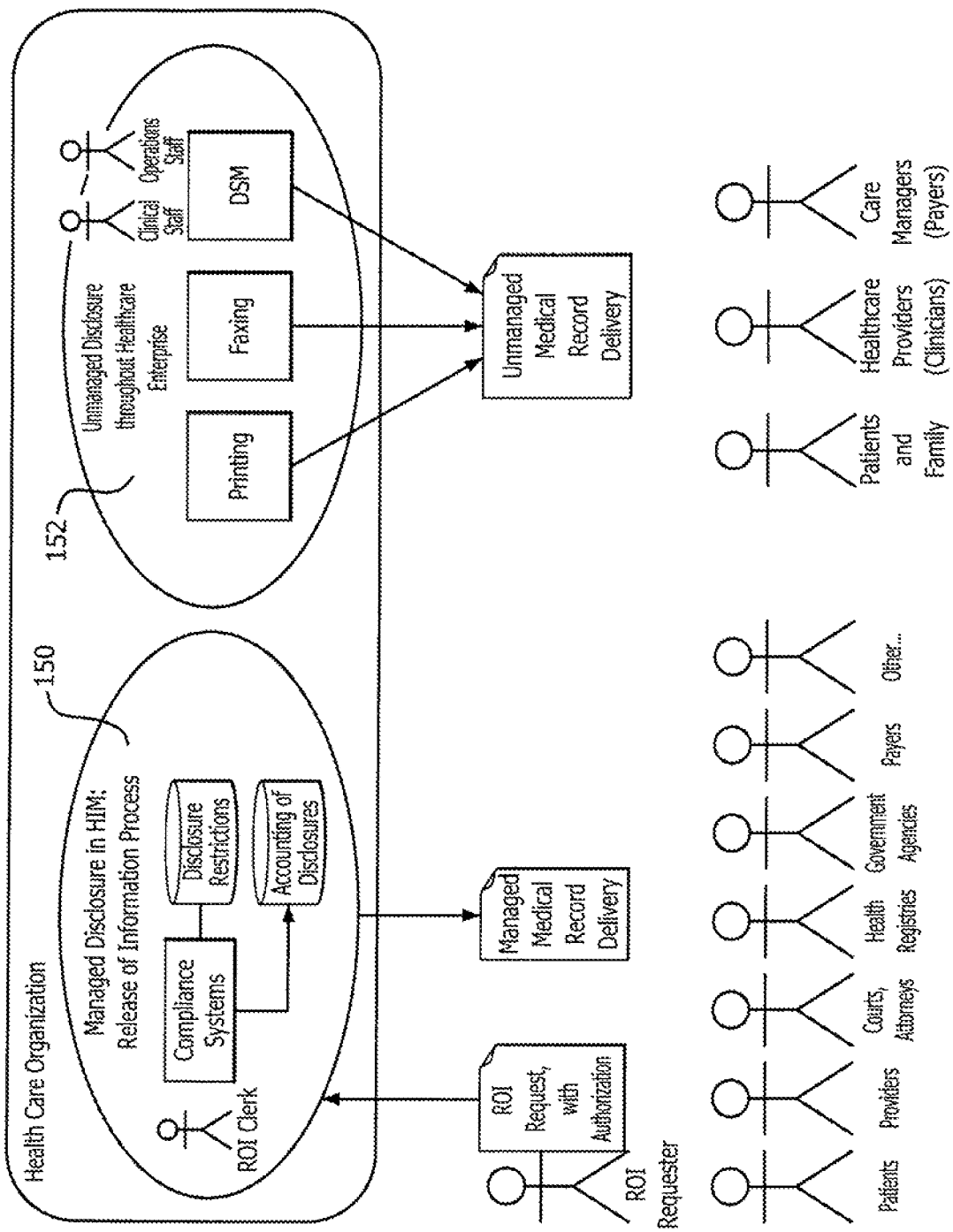
FIG. 1 shows a DSM within context of HCO Disclosure Management.
Figure 2:
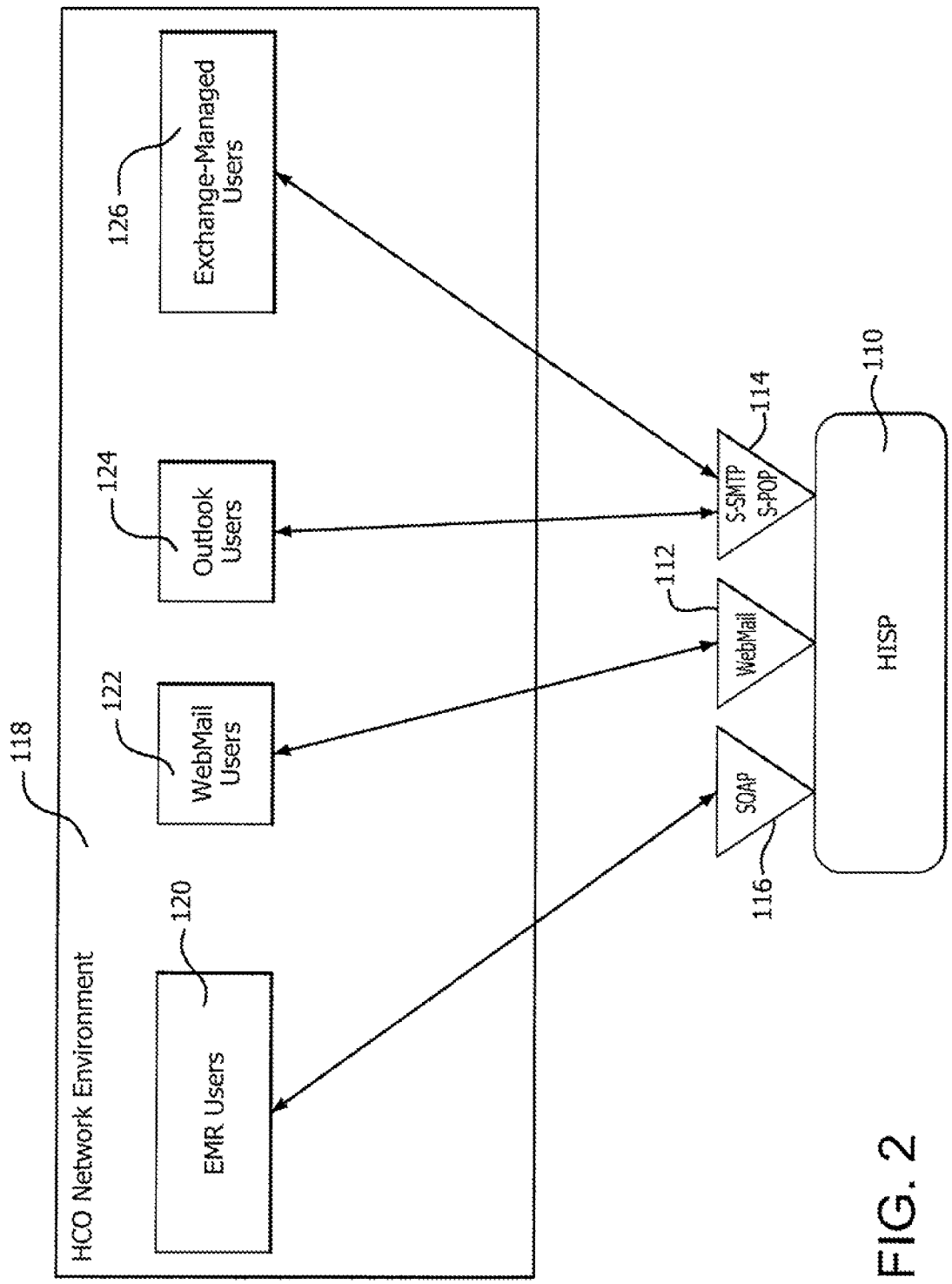
FIG. 2 shows the typical interconnectivity of a Healthcare Organization with its selected HISP.

Referring now to FIG. 2, in normal operation, an HCO selects a HISP 110 to manage its connectivity to other HCOs, via Direct. Secure Messaging (DSM). Typical interfaces for interconnectivity include two Internet standard interfaces include WebMail 112 and S-SMTP/S-POP/S-IMAP 114; as well as one interface that is healthcare industry specific: XDR/XDM over SOAP 116.

XDR, which stands for Cross-Enterprise Document Reliable Interchange, is a standard for securely sending messages containing Health Record documents from between a sending system, such as an EMR (Electronic Medical Records system), and a receiving system, which may also be an EMR. Within this standard, the document is wrapped in a secure XML container that includes metadata about both the document and the patient, and may also have a security section, with authentication and certificate exchange information to ensure that the exchange is secure.

XDM, which stands for Cross-Enterprise Document Media Interchange, is a standard for wrapping XDR messages within an S-MIME attachment to an e-mail message.

In the absence of a HISP proxy 10 (best seen in FIG. 3), a typical HCO Network Environment 118 includes EMR Users 120, Webmail Users 122, Outlook Users 124, and Exchange-Managed Users 126. In such an environment, an HCO will configure these different users and systems to connect to the HISP 110 in the most appropriate manner. Users 124 that have Outlook, or some other comparable e-mail client, can be configured for message sending and receiving via S-SMTP, S-POP, and S-IMAP protocols 114. Users 122 that have no e-mail client may use a WebMail 112 system provided by the HISP 110. Users 120 that have EMRs will generally send and receive XDR messages via SOAP endpoints 116 on the HISP and on the EMR.

2. Connectivity of the HISP when a HISP Proxy is Present HISP Interfaces

Figure 3:
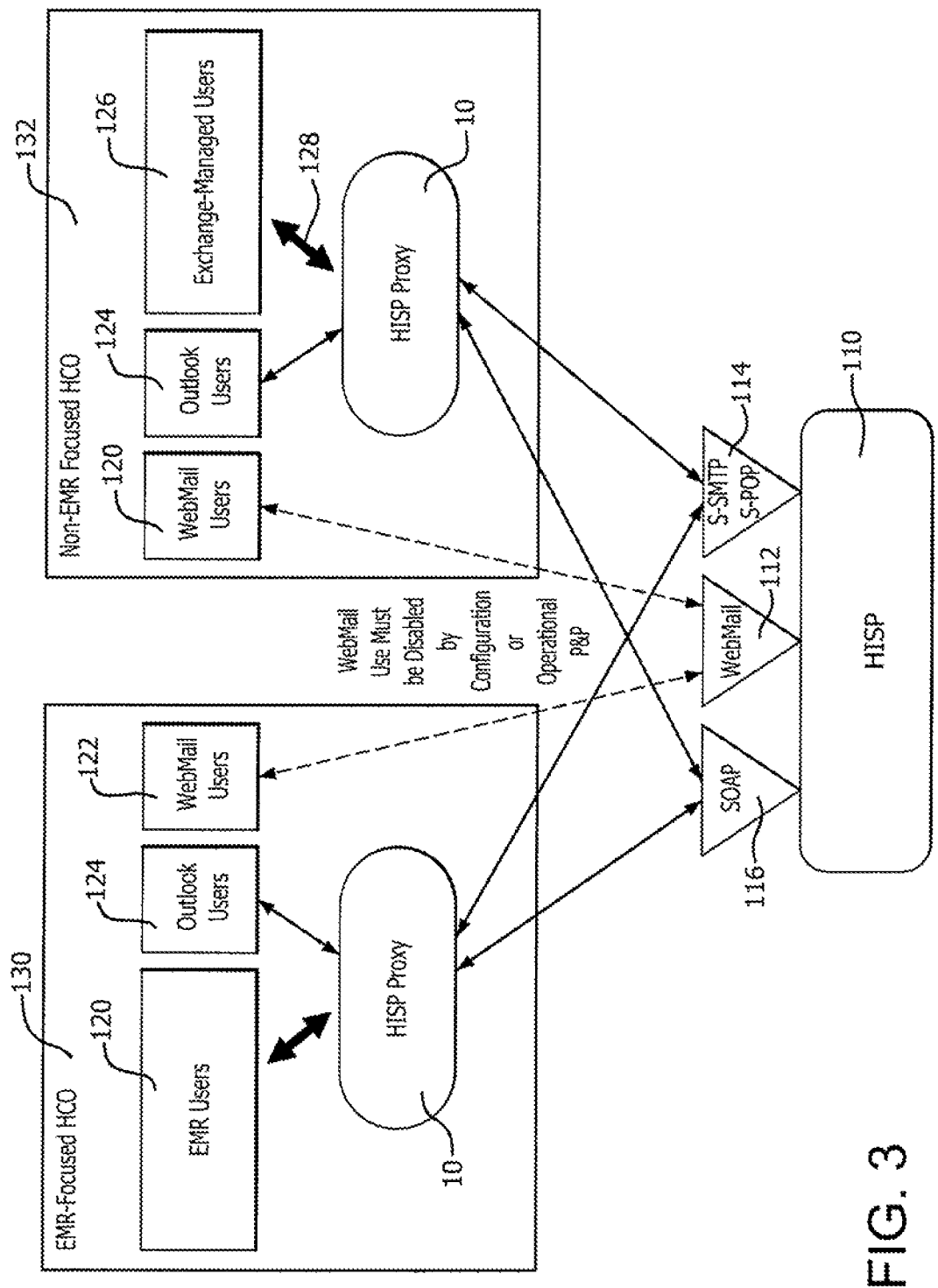
FIG. 3 shows HISP Proxy Interconnectivity of the present invention in EMR-focused and Non-EMR focused environments.

Referring now to FIGS. 2 and 3, The HISP Proxy 10 is designed primarily for two basic operating environments: EMR-focused DSM 130 and Non-EMR focused DSM 132.

In the EMR-focused DSM environment 120, the HCOs typically use DSM primarily through their EMRs by virtue of being covered under the Meaningful Use incentive programs, such as hospitals, health systems, and IDNs.

In the EMR-focused DSM environment 120, the HCOs typically do not use DSM primarily through their EMRs, either because they are not covered under Meaningful Use (such as Skilled Nursing facilities, Long-term Care facilities, Behavioral Health facilities), because EMRs are not their primary care management IT systems (such as national pharmacy corporations, home healthcare provider companies), or because they are managing healthcare across a wide variety of delivery settings (such as accountable care organizations).

Referring to FIG. 2, there are three types of interfaces that end-users in a HISP environment can use in order to send and receive messages: The DSM standard SOAP-based web service interface 116, provided by their EMR, Internet standard secure-transport e-mail protocols 114, including S-SMPT, S-POP and IMAPI 112, provided by an e-mail client, such as Microsoft Outlook, Browser-based WebMail over HTTPS, provided by the HISP.

Referring back to FIG. 3, in the HISP Proxy environment, an additional interface is added: A Microsoft. Exchange (or other e-mail management server) interface 128, for mapping regular organizational e-mail accounts with DSM e-mail accounts, provided by the HISP Proxy's Email Relay component.

The WebMail interface 112 is not used in the HISP Proxy environment, as there is no way to control the flow of DSM messages when users log in to the HISP's WebMail service.

Some HISPs can restrict the use of WebMail according to client desire (configured at the user or organizational level). Still others may not offer WebMail at all because of security concerns. If the HISP platform is not capable of restricting the use of WebMail, the HCO restricts its use by operational policy and procedure.

The types of DSM interfaces in use may overlap in the two operating environments, but in general, the EMR-focused. DSM 130 will be primarily through the DSM standard SOAP interface 116, and the non-EMR focused DSM will be through Internet standard secure-transport e-mail protocols 114. In both environments, HCOs will have an interest in controlling the access of end-users to the HISP, for reasons of compliance with HIPAA and other related laws and regulations.

Regardless of which interfaces are used to connect end-users to the HISP Proxy, a DSM Message Bus, described below, can be configured to connect to the HISP via SOAP or S-SMTP/S-POP, based on the preference of the HCO.

3. HISP Proxy Component Descriptions DSM Message Bus

Figure 4:
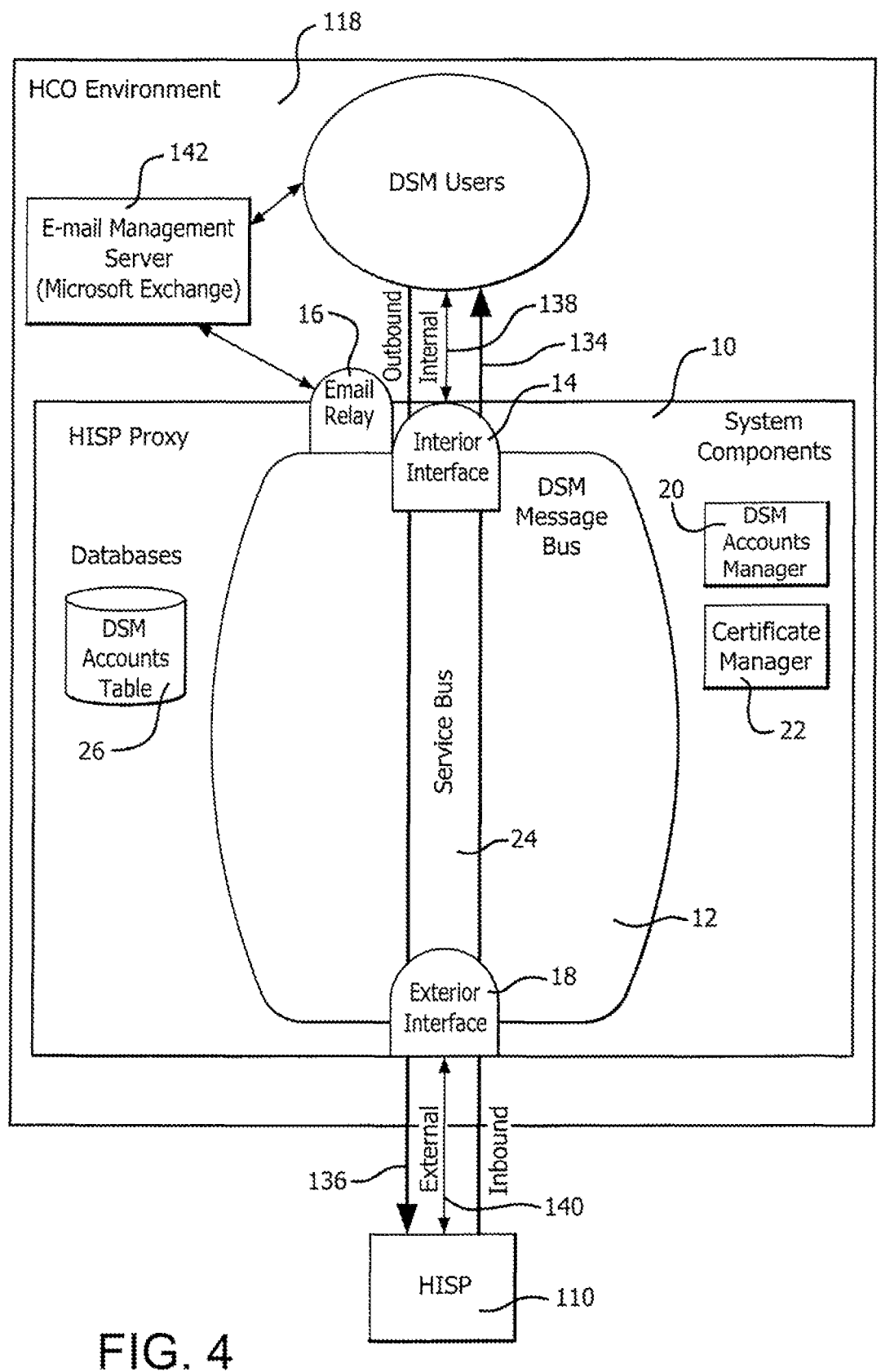
FIG. 4 shows a DSM Message Bus of the present invention.

As best seen in FIG. 4, the DSM Message Bus 12 provides the core functional capacity to sit between end-users within the HCO environment 118 and the HISP 110, to intercept inbound messages and outbound messages, to act upon them in a variety of ways that bring added functionality to the basic DSM service, and finally to pass the messages through.

Message traffic along the DSM Message Bus 12 takes place in two regular channels, an Inbound channel 134 and an Outbound channel 136; and two special channels, an Internal channel 138 and an External channel 140. The Inbound and Outbound messages are simply the normal flow of DSM from HCO end-user accounts to outside DSM endpoints. The special channels are for meta-communications for exceptional or service-specific purposes, such as: Negotiating specific user overrides to Disclosure Restrictions, and Enabling e-signatures to be affixed to document attachments to DSM messages. The operation of these special channels are described in more detail below, in context of the individual service module components.

The DSM Message Bus 12 has the folio wing sub-components: an Interior Interface 14 and an Email Relay 16, an. Exterior Interface 18, a User Accounts Manager 20, a Certificate Manager 22, and a Service Bus 24.

The Interior Interface 14 looks to the end-user as a HISP does: it comprises a SOAP server interface and an S-SMTP/S-POP/IMAPI interface. An Email Relay is included to interface with other non-DSM email servers, such as Microsoft Exchange Server 142. The Exchange Server authenticates via server-to-server authentication, which is incompatible with the HISP security protocols.

The Exterior interface 18 looks to the HISP as an end-user does: it mimics the interface behavior of a SOAP client, or an S-SMPT/S-POP/IMAPI client.

The Exterior Interface 18 can be configured to operate in one of three modes: Direct-standards only, in which case only the SOAP interface is used, regardless of how messages came in on the Interior Interface; Internet-standards only, in which case only the S-SMPT/S-POP/IMAPI interface is used; or Pass-through, in which case the type of connection used matches the interface used on the Interior Interface.

The DSM Accounts Manager 20 keeps track of all DSM user accounts and account configuration, and allows authentication to take place on the Interior Interface 14 and Exterior Interface 18. User account information is stored in a DSM Accounts table database 26.

The Certificate Manager 22 may or may not be needed, depending on whether the HCO uses Organization-Level certificates, or End-User Level certificates. Most private hospitals are expected to use Organizational-Level certificates for their DSM. If End-User Level certificates are needed, the Certificate Manager will manage these certificates, and keep them secure.

The development of Healthcare Message Content Standards in the Healthcare industry has led to opportunities around DSM: The CDA has a structure that makes it simple to extract metadata from the Medical Record, such as the Patient Name, Demographics, and the HCO's patient identifier. The HISP Proxy 10 leverages this metadata to assist with carrying out Compliance functions, such as Accounting of Disclosures and Patient Consent Management.

The Service Bus 24 allows an ordered chain of functional service components to be executed as messages pass through the DSM Message Bus 12, between the Interior interface 14 and the Exterior interface 18. A fully non-configured Service Bus 24 looks to the end-user just as though they had connected directly to the HISP 110, and were sending and receiving messages without interception. In addition, services can be added to the chain to provide additional DSM functionality to the HCO.

Figure 5:
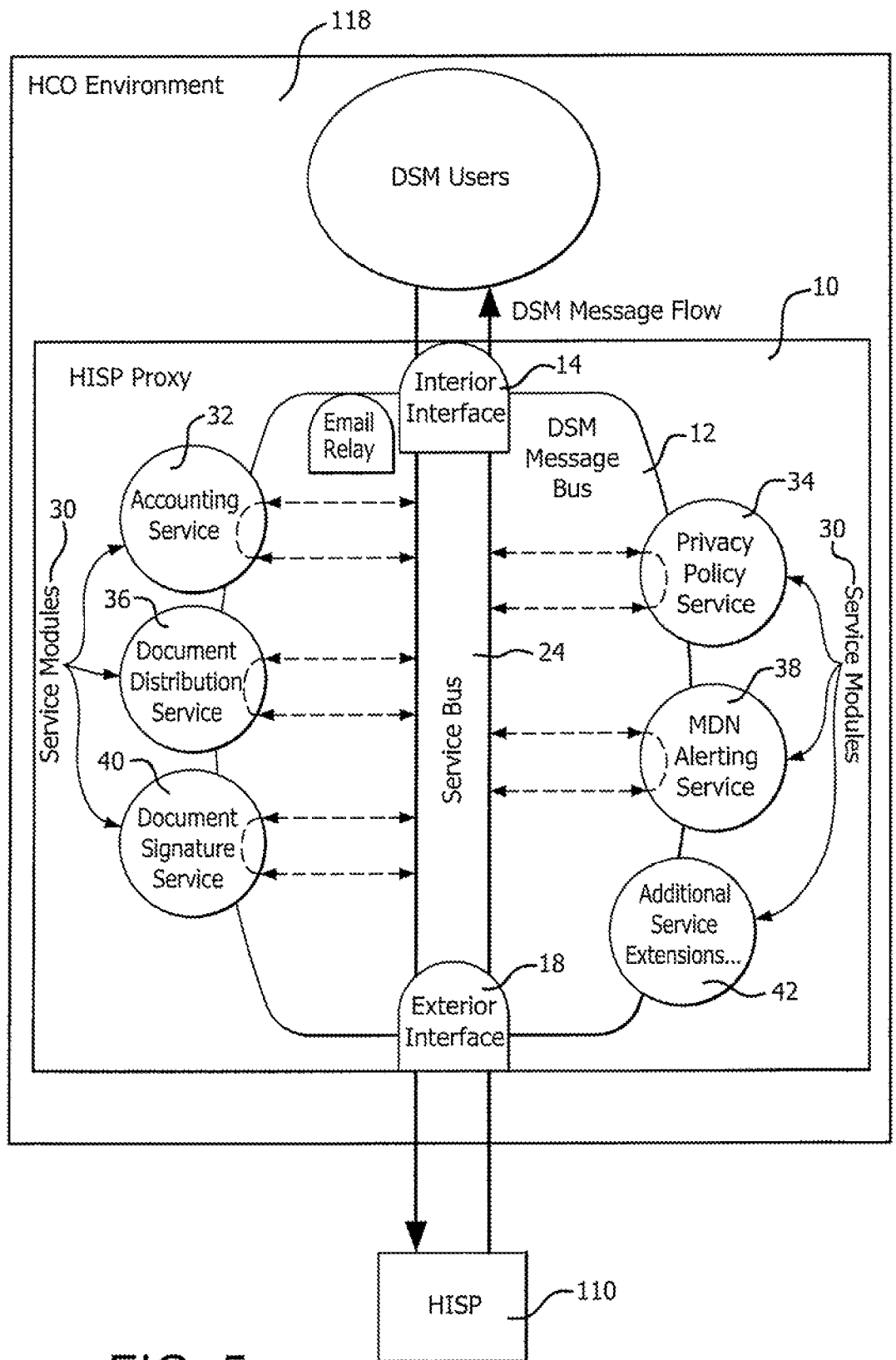
FIG. 5 shows how HISP Proxy services are rendered along the DSM Message Bus, via a modular and extensible value-added Service Bus.

Referring now to FIG. 5, along the DSM Message Bus 12 are component service modules 30 that create value-added functionality. These service modules 30 include, but are not limited an Accounting Service 32, a Privacy Policy Service 34, a Document Distribution Service 36, a MSN Alerting Service 38, and a Document Signature Service 40.

Furthermore, because all DSM disclosure traffic flows through the DSM Message Bus 12, the HISP Proxy 10 design lends itself to layering in additional functional components 42 as demand and opportunity arise.

3.1 Accounting Service

Figure 6:
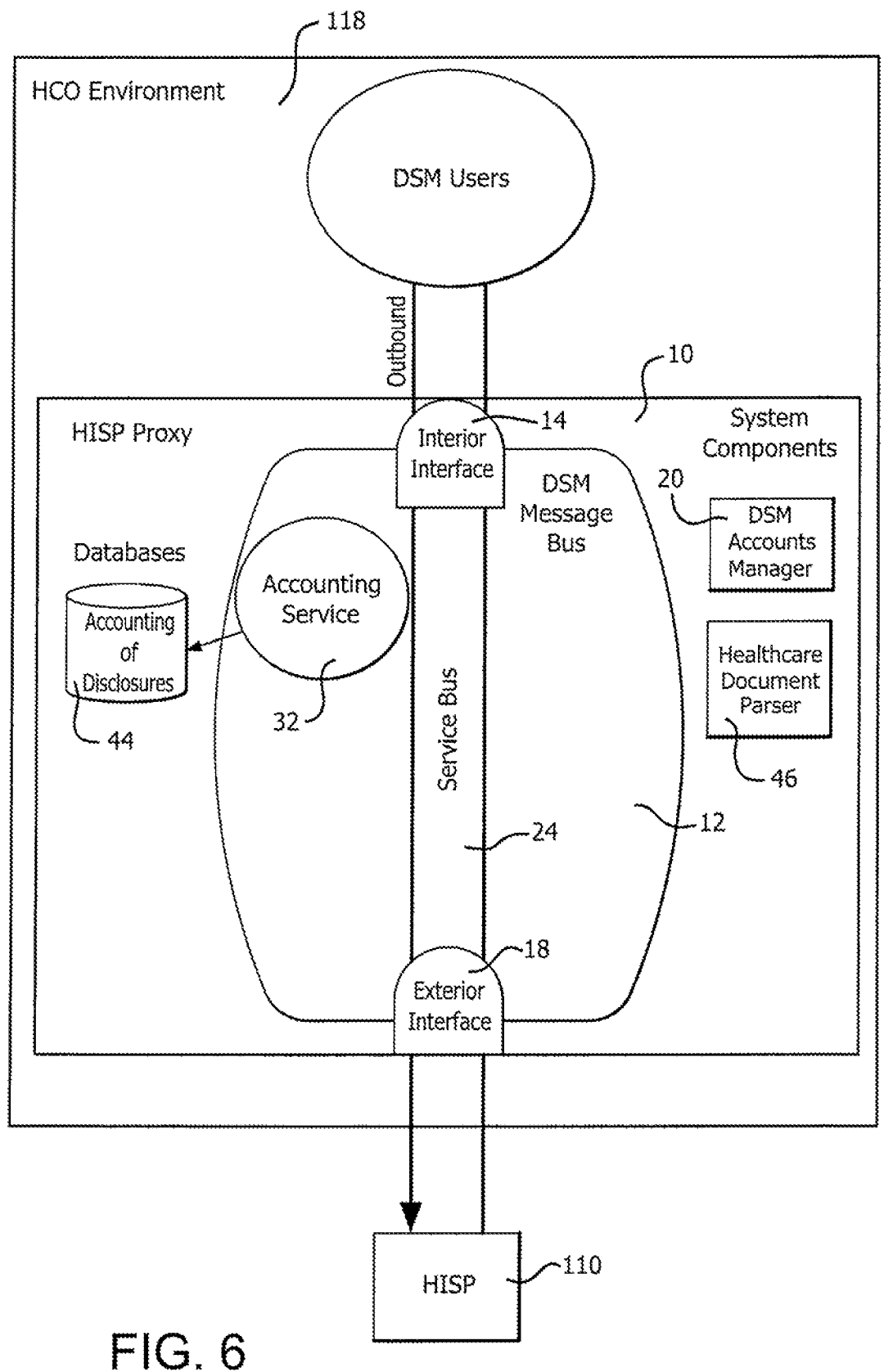
FIG. 6 shows an Accounting Service of the present invention.

Referring to FIG. 6, the Accounting Service 32 provides the HIPAA required Accounting of Disclosures (AoD) 44. It parses outbound message attachments to determine the patient whose information is being disclosed, and records the necessary data elements for the AoD in database 44. These elements include: the patient whose PHI is disclosed; the reason for the disclosure; and Disclosure information, including who made the disclosure (the sending party), the date of the disclosure, the recipient, and what sort of information was disclosed.

The Accounting System 32 relies on a Healthcare Document Parser 46, which uses Clinical Document Architecture (CDA) standards to enable it to read metadata associated within documents that are passed as attachments or within XOR messages. The system can be configured to infer information about the reason for disclosure based on the sending party's configuration in the end-users table (the DSM Accounts Manager 20 manages this table).

3.2 Privacy Policy Service

Figure 7:
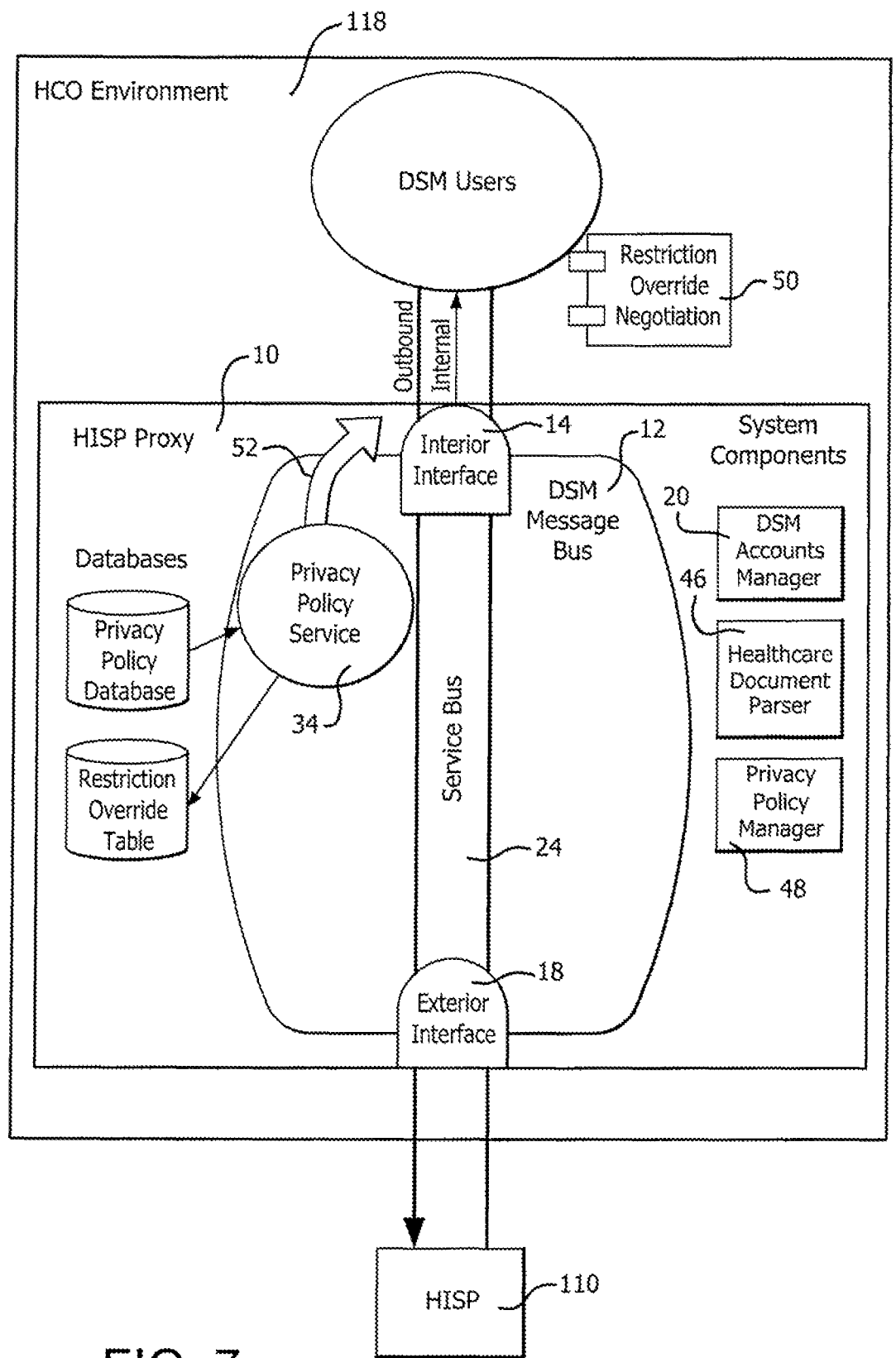
FIG. 7 shows a Privacy Policy Service of the present invention.

Referring to FIG. 7, the Privacy Policy Service 34 provides compliance with Disclosure Restrictions. It is configured with hospital policy (using a database-driven Privacy Policy Manager 48), and tracks patient restrictions on their PHI. These restrictions may be integrated with healthcare standard Basic Patient Privacy Consent (BPPC) documents maintained by the HCO in other systems that can be configured to automatically send BPPC updates to the HISP Proxy 10.

If a DSM message is sent for a patient with restrictions, or if the DSM message is found to otherwise be non-compliant, it sends an alert 50 to the DSM end-user sending the message, who can elect to override the restriction. This override is recorded in a log. These alert messages 50 are not passed along the normal Inbound or Outbound message bus. Rather they utilize an Internal Message bus 52 that allows for communication between the Service Module 34 and the sending user.

3.3 Document Distribution Service

Figure 8:
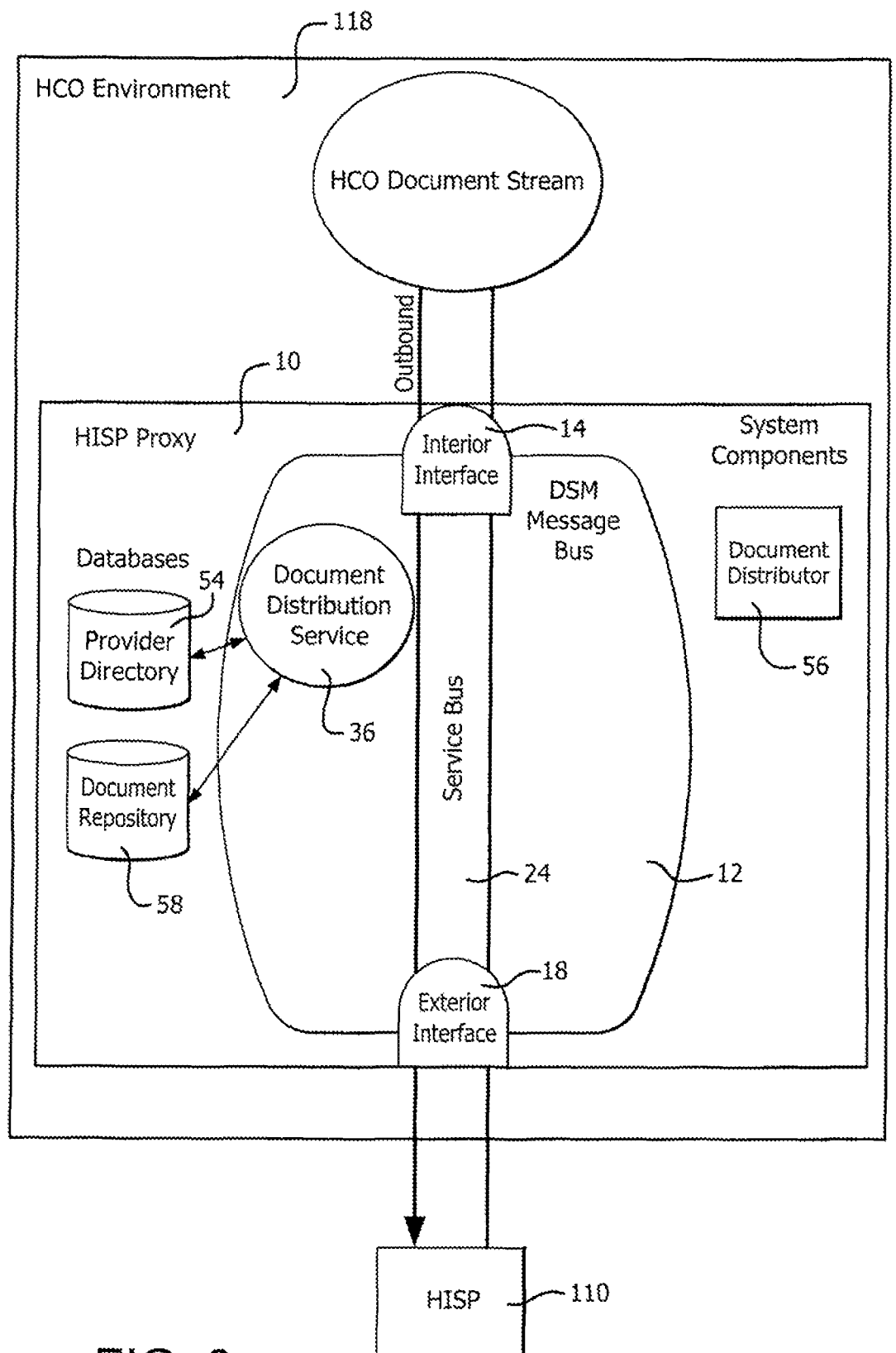
FIG. 8 shows a Document Distribution Service of the present invention.

Referring to FIG. 8, the Document Distribution Service 36 is a special mechanism to meet a need that hospitals have to distribute patient health records to other providers, especially at the time the patient is discharged. A special interface 58 is set up within hospital HIT systems containing the documents to be distributed. Metadata is included with this, to specify which healthcare provider to send the documents to.

A Document Distributor 56 receives the documents to be distributed, and then sends them along one of four distribution paths, depending on the preference of the intended recipient: DSM, Fax, Email notification with a secure pickup link, and an Exception queue, for manual processing of those recipients for whom no DSM endpoint, fax number, or regular email address is provided.

A Provider Directory 54 is used to match recipients with their preferred method of receiving messages. This Provider Directory 54 is built by a combination of metadata associated with the HCO Document Stream, manually entered provider preferences using a web portal interface by HCO administrators of this service, and via manual exception queue processing for recipients without destination endpoints (fax, DSM, or email) available.

A pickup portal (not shown) is provided for Email notification with a secure pickup link. The email contains a link which is used to pick up the document using HTTPS/SSL.

3.4 MDN Alerting Service

Figure 9:
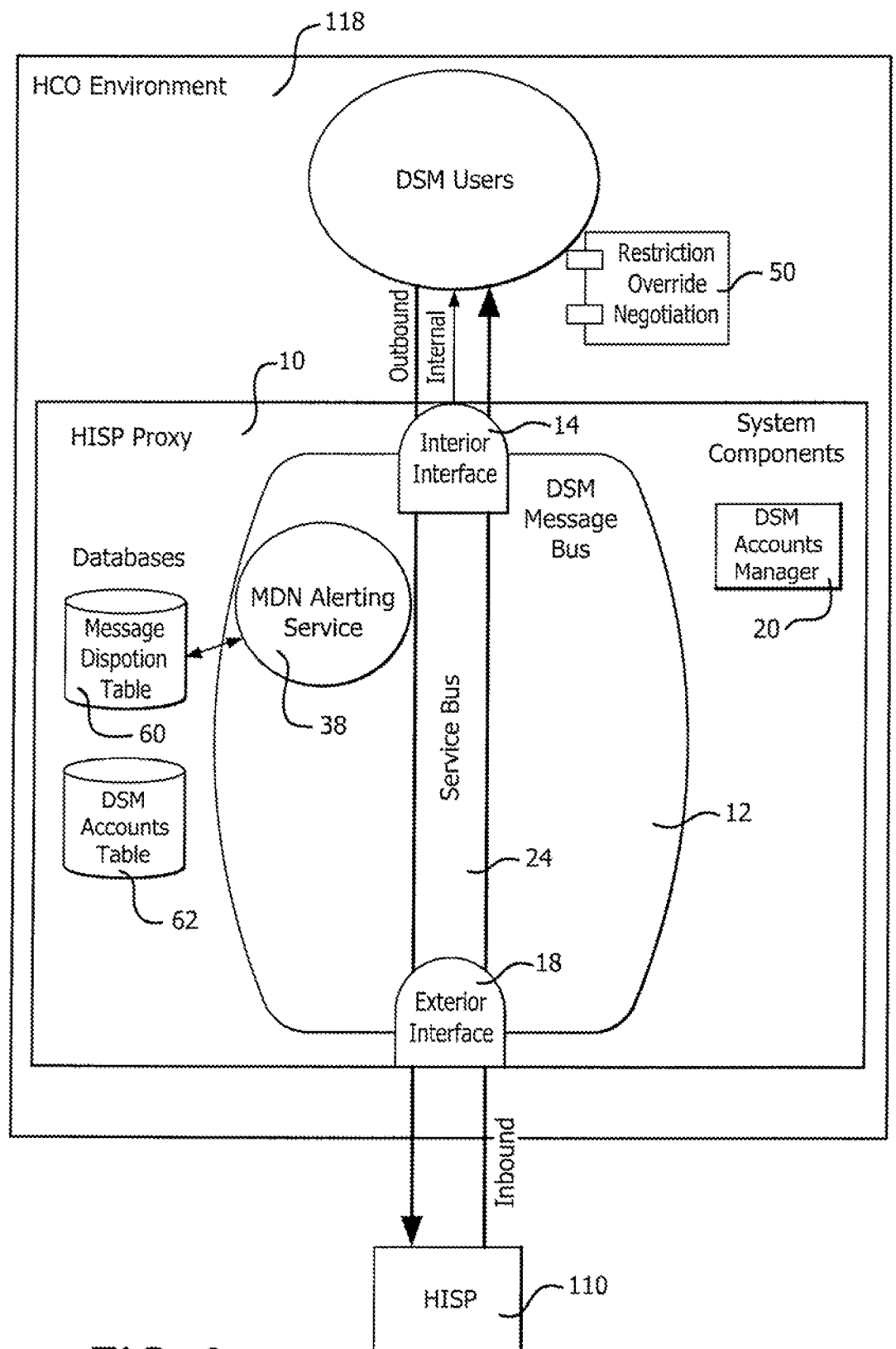
FIG. 9 shows an MDN Alerting Service of the present invention.

Referring to FIG. 9, The MDN Alerting Service 38 provides structure around MDN messages (the DSM version of return receipts), which are mandatory for all messages in the DSM environment, and which can be overwhelming to a user. Because of the importance of knowing when messages are not delivered or read, and because of the difficulty of managing DSM messages, the MDN Alerting service 38 allows a sending end-user to configure preferences for when they wish to be alerted when messages have taken too long to be delivered to or read by their intended recipient.

The preferences are configured in a DSM Accounts table 62, and outbound DSM messages are tracked in a Message Disposition table 60. When MDNs are received through the Inbound channel, message status changes to Delivered, and then Read. Failures are notified immediately, and messages which take too long to be delivered result in notifications after their timeout period. The notification messages take place on the Internal message channel 52, shown in FIG. 7.

3.5 Document Signing Service

Figure 10:
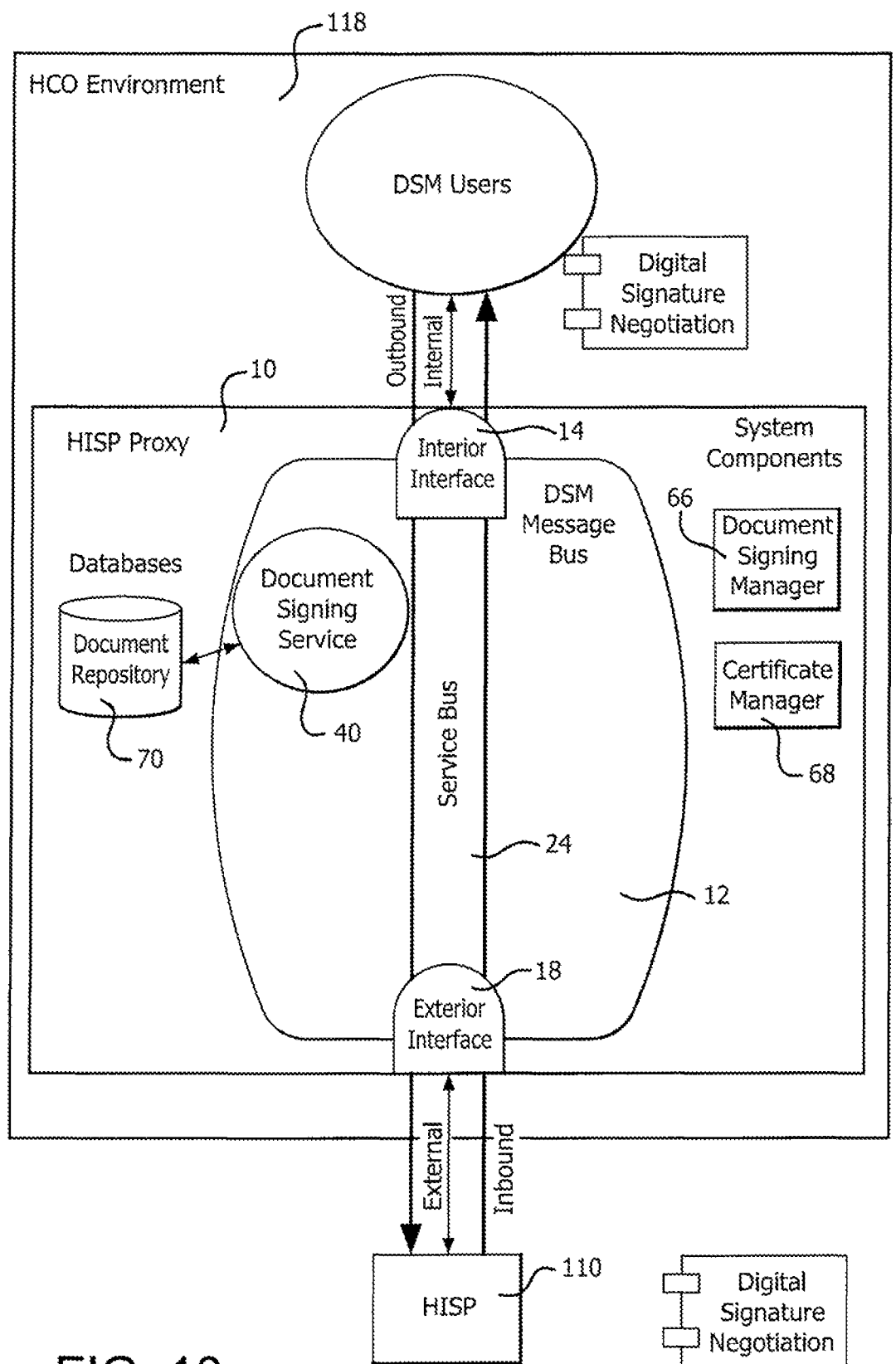
FIG. 10 shows a Document Signing Service of the present invention.

Referring to FIG. 10, the Document Signing Service 40 enables patient health record documents to be sent to clinicians for electronic signature. The document may be signed by clinicians within the HCO, or by outside clinicians.

The signing process begins with a request for a Signature Negotiation to be created. This document to be signed is saved in a Document Repository 70, and a signing request message is sent to the clinician. The Internal 138 and External 136 message channels are used for the signing request message, depending on whether the signing user is within the HCO or outside. The document signing is managed by a Document Signing Manager 66.

The clinician clicks on a link which takes them to a web portal where they can view the document, and affix their electronic or digital signature. Digital signatures require a special level of setup, and the certificates are managed within the HISP Proxy 10 by a Certificate Manager 68.

The document, once signed, can be distributed with the signature via the HISP 10.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for a Health Information Service Providers Proxy (HISP) for Electronic Medical Records (EMR)-focused and Non-EMR focused environments for healthcare organizations (HCOs) to manage their Direct Secure Messaging (DSM) and HISP communications comprising the steps of:
providing a DSM message bus located between HCO end-users and a HISP, the DSM Message Bus having an interior interface having a Simple Object Access Protocol (SOAP) server interface and an Simple Mail Transfer Protocol Secure (S-SMTP)/Simplified Post Office Protocol (S-POP)/Internet Message Access Protocol Interface (IMAPI) interface, an email relay, an exterior interface, and a Service Bus in communication with the interior interface and the exterior interface; an accounting service; a privacy policy service; and a document distribution service;
intercepting inbound messages with the DSM Message Bus and then passing the messages there through;
using the interior interface to interface with DSM users;
using the email relay to interface with other non-DSM users;
using the exterior interface to interface with the HISP and mimicking the interface behavior of SOAP clients or the S-SMPT/S-POP/IMAPI clients;
executing an ordered chain of functional service components by the Service Bus in communication with the interior interface and the exterior interface as messages pass through the DSM Message Bus;
providing Accounting of Disclosures (AoD) by the accounting service in accordance with the accounting service providing protected health information, and parsing via the accounting service outbound message attachments to determine an identity of a patient whose information is being disclosed and recording patient related data for the AoD in a database;
providing compliance with disclosure restrictions via the privacy policy service, the privacy policy service being configured with hospital policy;
tracking patient restrictions via the private policy service; and
receiving the documents to be distributed via the document distribution service and sending the documents to an intended recipient via DSM, Fax, Email notification with a secure pickup link, or an Exception queue.

2. The HISP Proxy managing method according to claim 1 further providing a Message Disposition Notifications (MDN) alerting service that allows a sending end-user and configuring preferences when messages have not been delivered to or read by their intended recipient according to a time configured by the user.

3. The HISP Proxy managing method according to claim 1 further providing a document signing service, the document signing service sending patient health record documents to clinicians for electronic signature, internal and/or external message channels are used for a signing request message.

4. The HISP Proxy managing method according to claim 1 further providing a document signing service, the document signing service sending patient health record documents to clinicians for electronic signature, internal and/or external message channels are used for a signing request message.

5. The HISP Proxy managing method according to claim 3 wherein the document distribution service further includes a provider directory and further comprising the step of matching recipients with their preferred method of receiving messages.

6. The HISP Proxy managing method according to claim 1 wherein the DSM message bus further comprises a DSM accounts manager to keep track of DSM user accounts and account configuration data, authentication taking place on the Interior Interface and Exterior Interface.

7. The HISP Proxy managing method according to claim 4 wherein the DSM message bus further comprises a DSM accounts manager to keep track of DSM user accounts and account configuration data, authentication taking place on the interior interface and the exterior interface.

8. The HISP Proxy managing method according to claim 1 wherein the DSM message bus further comprises a certificate manager and further comprising the step of managing and keeping secure End-User Level certificates.

9. The HISP Proxy managing method according to claim 7 wherein the DSM message bus further comprises a certificate manager and further comprising the step of managing and keeping secure End-User Level certificates.

10. The HISP Proxy managing method according to claim 1 wherein the DSM message bus further comprising an Inbound channel and an Outbound channel for transmitting message traffic between the DSM users and the HISP, and an Internal channel and an external channel to transmit meta-communications for service-specific purposes.

11. The HISP Proxy managing method according to claim 9 wherein the DSM message bus further comprising an Inbound channel and an Outbound channel for transmitting message traffic between the DSM users and the HISP, and the internal channel and the external channel transmit meta-communications for service-specific purposes.

12. The HISP Proxy managing method according to claim 1 further providing an e-mail management server interface and further comprising the step of mapping regular organizational e-mail accounts with DSM e-mail accounts, provided by the HISP Proxy's Email Relay component.

13. The HISP Proxy managing method according to claim 11 further providing an e-mail management server interface and further comprising the step of mapping regular organizational e-mail accounts with DSM e-mail accounts, provided by the HISP Proxy's Email Relay component.

14. The HISP Proxy managing method according to claim 1 wherein the accounting system further comprises a healthcare document parser and further comprising the step of reading metadata associated within documents that are passed as attachments or within Cross-Enterprise Document Reliable (XDR) messages.

15. The HISP Proxy managing method according to claim 13 wherein the accounting system further comprises a healthcare document parser and further comprising the step of reading metadata associated within documents that are passed as attachments or within Cross-Enterprise Document Reliable messages.

16. The HISP Proxy managing method according to claim 1 wherein the exception queue comprises a component to manually process physical documents to be distributed and then sends the physical documents to an intended recipient.

* * * * *